United States Patent
Beane et al.

(10) Patent No.: US 9,468,515 B2
(45) Date of Patent: Oct. 18, 2016

(54) METHOD AND APPARATUS FOR EFFECTING A PERCUTANEOUS AORTIC VALVE BYPASS

(75) Inventors: Richard M. Beane, Hingham, MA (US); James Alan Crunkleton, Weston, MA (US); Anthony Liepert, Lincoln, MA (US); Joseph L. Smith, Jr., Concord, MA (US)

(73) Assignee: Correx, Inc., Dedham, MA (US)

( * ) Notice: Subject to any disclaimer, the term of this patent is extended or adjusted under 35 U.S.C. 154(b) by 0 days.

(21) Appl. No.: 12/829,246

(22) Filed: Jul. 1, 2010

(65) Prior Publication Data
US 2011/0118651 A1 May 19, 2011

Related U.S. Application Data

(60) Provisional application No. 61/222,180, filed on Jul. 1, 2009.

(51) Int. Cl.
*A61F 2/06* (2013.01)
*A61F 2/24* (2006.01)
(Continued)

(52) U.S. Cl.
CPC .......... *A61F 2/064* (2013.01); *A61F 2/2418* (2013.01); *A61F 2/2475* (2013.01); *A61F 2/82* (2013.01); *A61F 2220/0016* (2013.01)

(58) Field of Classification Search
CPC .......... A61M 27/002; A61M 1/3655; A61M 5/14276; A61M 5/00; A61F 2/064; A61F 2/06; A61F 2/24; A61F 2/82; A61F 2/04; A61F 2/2418; A61F 2/2475; A61F 2220/0016
USPC ........ 604/9, 8; 600/36; 623/1.13, 1.14, 1.24, 623/1.3, 1.35, 1.36, 3.1, 23.64, 23.68, 23.7, 623/902–904, 914, 1.26, 2.14, 2.17, 900
See application file for complete search history.

(56) References Cited

U.S. PATENT DOCUMENTS 3,657,744 A * 4/1972 Ersek .................. A61B 17/11
128/898
4,118,806 A 10/1978 Porier et al.
(Continued)

FOREIGN PATENT DOCUMENTS

EP 1 599 151 11/2005
EP 2 111 243 6/2008

OTHER PUBLICATIONS

Brown, John W. et al., Apicoaortic Valved Conduits for Complex Left Ventricular Outflow Obstruction: Technical Considerations and Current Status, The Annals of Thoracic Surgery, Aug. 1984, pp. 161-168, vol. 38, No. 2.
(Continued)

*Primary Examiner* — Loan H Thanh
*Assistant Examiner* — Andrew S Lo
(74) *Attorney, Agent, or Firm* — Pandiscio & Pandiscio

(57) ABSTRACT

A method for performing a percutaneous valve bypass, the method comprising providing a bypass conduit having a first end and a second end; connecting the first end of the bypass conduit to a first vascular structure at a first anastomosis; connecting the second end of the bypass conduit to a second vascular structure at a second anastomosis; advancing a percutaneous valve along the bypass conduit to a deployment site located within the bypass conduit; and deploying the percutaneous valve at the deployment site so that fluid is permitted to pass from the second vascular structure to the first vascular structure but is prevented from passing from the first vascular structure to the second vascular structure.

20 Claims, 8 Drawing Sheets

(51) Int. Cl.
*A61M 5/00* (2006.01)
*A61F 2/82* (2013.01)

(56) References Cited

U.S. PATENT DOCUMENTS

| | | | | |
|---|---|---|---|---|
| 6,090,140 | A * | 7/2000 | Gabbay | A61B 17/11 623/2.1 |
| 6,893,460 | B2 * | 5/2005 | Spenser et al. | 623/2.14 |
| 7,077,801 | B2 * | 7/2006 | Haverich | 600/16 |
| 7,452,374 | B2 * | 11/2008 | Hain et al. | 623/1.44 |
| 7,510,561 | B2 | 3/2009 | Beane et al. | |
| 7,766,811 | B2 | 8/2010 | Haverich | |
| 2003/0120331 | A1 * | 6/2003 | Chobotov et al. | 623/1.13 |
| 2004/0116769 | A1 | 6/2004 | Jassawalla et al. | |
| 2004/0186559 | A1 * | 9/2004 | Perouse | 623/1.31 |
| 2005/0149093 | A1 * | 7/2005 | Pokorney | 606/185 |
| 2005/0222674 | A1 * | 10/2005 | Paine | 623/1.24 |
| 2006/0142848 | A1 * | 6/2006 | Gabbay | 623/1.26 |
| 2006/0155239 | A1 * | 7/2006 | Knudson et al. | 604/9 |
| 2006/0161193 | A1 * | 7/2006 | Beane et al. | 606/185 |
| 2007/0055357 | A1 * | 3/2007 | Pokorney et al. | 623/1.26 |
| 2007/0208210 | A1 * | 9/2007 | Gelfand et al. | 600/16 |
| 2007/0265643 | A1 * | 11/2007 | Beane et al. | 606/153 |
| 2008/0200975 | A1 * | 8/2008 | Dubson | 623/1.15 |
| 2009/0076587 | A1 * | 3/2009 | Cully et al. | 623/1.13 |
| 2009/0082778 | A1 * | 3/2009 | Beane et al. | 606/108 |
| 2009/0125098 | A1 * | 5/2009 | Chuter | 623/1.26 |
| 2010/0114306 | A1 | 5/2010 | Lenihan et al. | |
| 2011/0118763 | A1 | 5/2011 | Beane et al. | |

OTHER PUBLICATIONS

Cooley, Denton A. et al., Apicoaortic Conduit for Left Ventricular Outflow Tract Obstruction: Revisited, The Society of Thoracic Surgeons, 2000, pp. 1511-1514, vol. 69.

* cited by examiner

METHOD AND APPARATUS FOR EFFECTING A PERCUTANEOUS AORTIC VALVE BYPASS

REFERENCE TO PENDING PRIOR PATENT APPLICATION

This patent application claims benefit of prior U.S. Provisional Patent Application Ser. No. 61/222,180, filed Jul. 1, 2009 by Richard M. Beane et al. for PERCUTANEOUS AORTIC VALVE BYPASS, which patent application is hereby incorporated herein by reference.

FIELD OF THE INVENTION

This invention relates to surgical methods and apparatus in general, and more particularly to surgical methods and apparatus for effecting a percutaneous aortic valve bypass.

BACKGROUND OF THE INVENTION

Percutaneous Valve Therapy (PVT), as currently under development by Edwards Lifesciences and Medtronic CoreValve, holds the promise of relieving critical aortic valve stenosis with a minimally invasive, "beating heart" procedure.

More particularly, in patients with critical aortic valve stenosis, the native valve's leaflets are generally calcified so that the effective area of the valve is greatly reduced, e.g., to an effective area of less than 1 cm$^2$. As a result, valve function is significantly impaired and the flow of oxygenated blood to the body is greatly reduced.

Percutaneous valve therapy (PVT) offers one promising solution to critical aortic valve stenosis. More particularly, with PVT, the diseased native valve is first manipulated so as to increase its flow area. This is typically done via valvuloplasty, where a stiff balloon is inflated inside the native valve so as to swage the leaflets open, thereby relieving the stenosis. Next, a prosthetic aortic valve is percutaneously deployed (e.g., endoluminally or via a thoracotomy) at the site of the native aortic valve, while the heart is still beating, in order to replace the malfunctioning natural aortic valve.

While PVT offers substantial advantages over a conventional "open heart" aortic valve replacement, it still suffers from a number of serious problems. More particularly, to date, deployment of percutaneous valves to the diseased native valve site has resulted in serious complications, such as:

1. Conduction system damage (i.e., damage to the electrical system of the heart), typically requiring installation of a permanent pacemaker (occurring in approximately 7% of patients);
2. Stroke (occurring in approximately 2.5% of patients);
3. Significant aortic regurgitation (occurring in approximately 4.7% of patients);
4. Valve malposition (occurring in approximately 1.5% of patients);
5. The need for conversion to conventional "open heart" surgery during the percutaneous procedure (occurring in approximately 2.7% of patients); and
6. Coronary obstruction (occurring in approximately 0.6% of patients).

The evolution of percutaneous valve deployment methods, as is well documented in the literature, has progressed in the following order:

1. "Antegrade deployment", where the prosthetic valve is advanced up through the venous system and across the septum of the heart to the native valve location. This method is generally no longer practiced.
2. "Retrograde deployment", where the prosthetic valve is advanced up from the femoral artery, over the aortic arch, to the native valve location.
3. "Transapical deployment", where the prosthetic valve is advanced through the apex of the heart, into the left ventricle and up to the native aortic valve location. Note that a thoracotomy is required in order to access the apex of the heart.

While PVT complication rates have slowly declined, the inherent disadvantages of manipulating the diseased native valve, and then deploying the prosthetic valve to the native valve location, are inescapable.

A known alternative to both conventional "open heart" aortic valve replacement, and to the aforementioned percutaneous valve therapy (PVT), is aortic valve bypass. In aortic valve bypass, a bypass conduit, having a prosthetic valve incorporated therein, is deployed between the left ventricle of the heart and the descending aorta. See, for example, FIG. 1. See also U.S. Pat. No. 7,510,561, issued Mar. 31, 2009 to Richard M. Beane et al. for APPARATUS AND METHOD OF CONNECTING A CONDUIT TO A HOLLOW ORGAN, which patent is hereby incorporated herein by reference.

As currently practiced, aortic valve bypass is a proven procedure that can relieve critical aortic stenosis without the aforementioned complications of percutaneous valve deployment to the native valve site (i.e., without the complications associated with PVT).

A drawback of current aortic valve bypass therapy, however, is the approximately 6"-8" thoracotomy incision which is required in order to gain access to the left ventricle of the heart and to the descending aorta, which is required in order to install the bypass conduit. As a result, aortic valve bypass cannot currently be considered to be a minimally invasive procedure, due to the need to provide a thoracotomy of such size. Also, when the ribs are spread to create access to the thoracic cavity, the ribs can sometimes fracture, thereby causing additional trauma to the patient.

Consequently, there is a need for an improved procedure to relieve critical aortic stenosis.

SUMMARY OF THE INVENTION

These and other objects of the present invention are addressed by the provision and use of a novel method and apparatus for effecting a percutaneous aortic valve bypass.

In one form of the invention, there is provided a method for performing a percutaneous valve bypass, the method comprising:

providing a bypass conduit having a first end and a second end;

connecting the first end of the bypass conduit to a first vascular structure at a first anastomosis;

connecting the second end of the bypass conduit to a second vascular structure at a second anastomosis;

advancing a percutaneous valve along the bypass conduit to a deployment site located within the bypass conduit; and deploying the percutaneous valve at the deployment site so that fluid is permitted to pass from the second vascular structure to the first vascular structure but is prevented from passing from the first vascular structure to the second vascular structure.

In another form of the invention, there is provided an apparatus for performing a percutaneous valve bypass, the apparatus comprising:

a bypass conduit comprising a first end for connection to a first vascular structure and a second end for connection to a second vascular structure; and a percutaneous valve for disposition at a deployment site within the bypass conduit so that fluid is permitted to pass from the second vascular structure to the first vascular structure but is prevented from passing from the first vascular structure to the second vascular structure.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Percutaneous Aortic Valve Bypass

Figure 1:
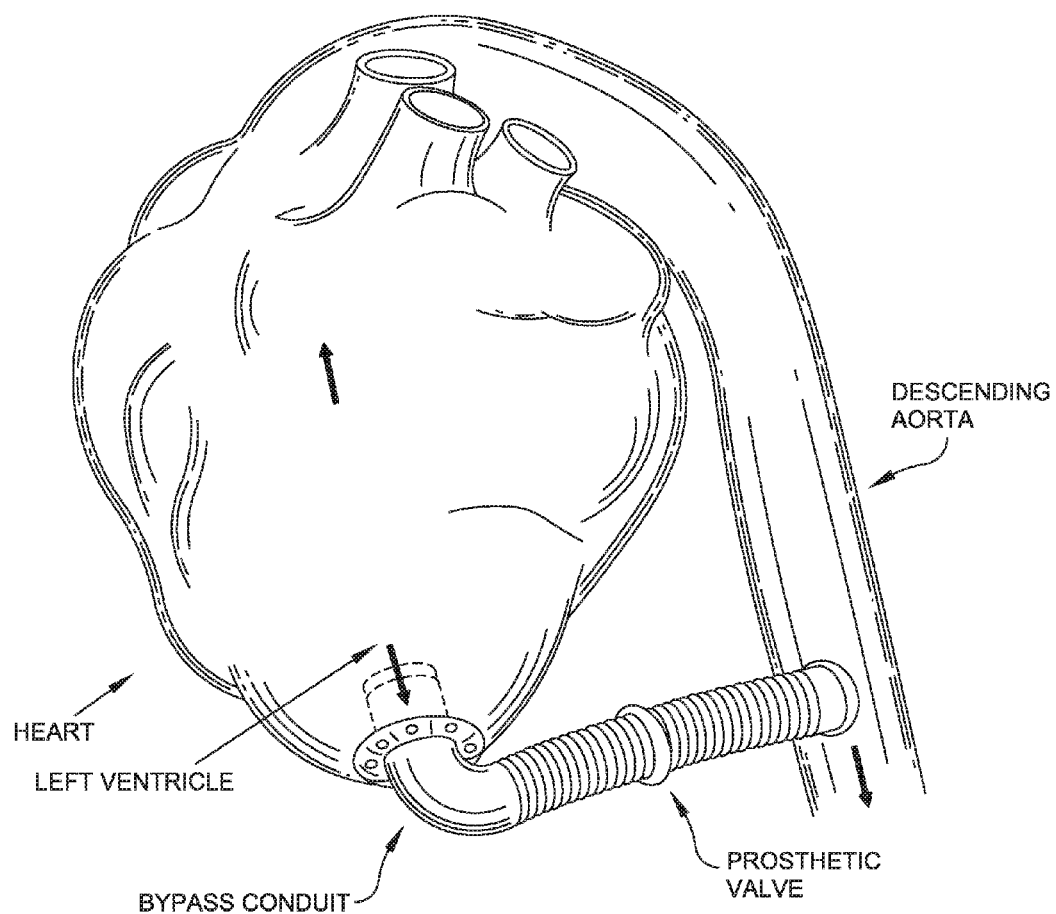
FIG. 1 is a schematic view showing an aortic valve bypass.
Figure 2:
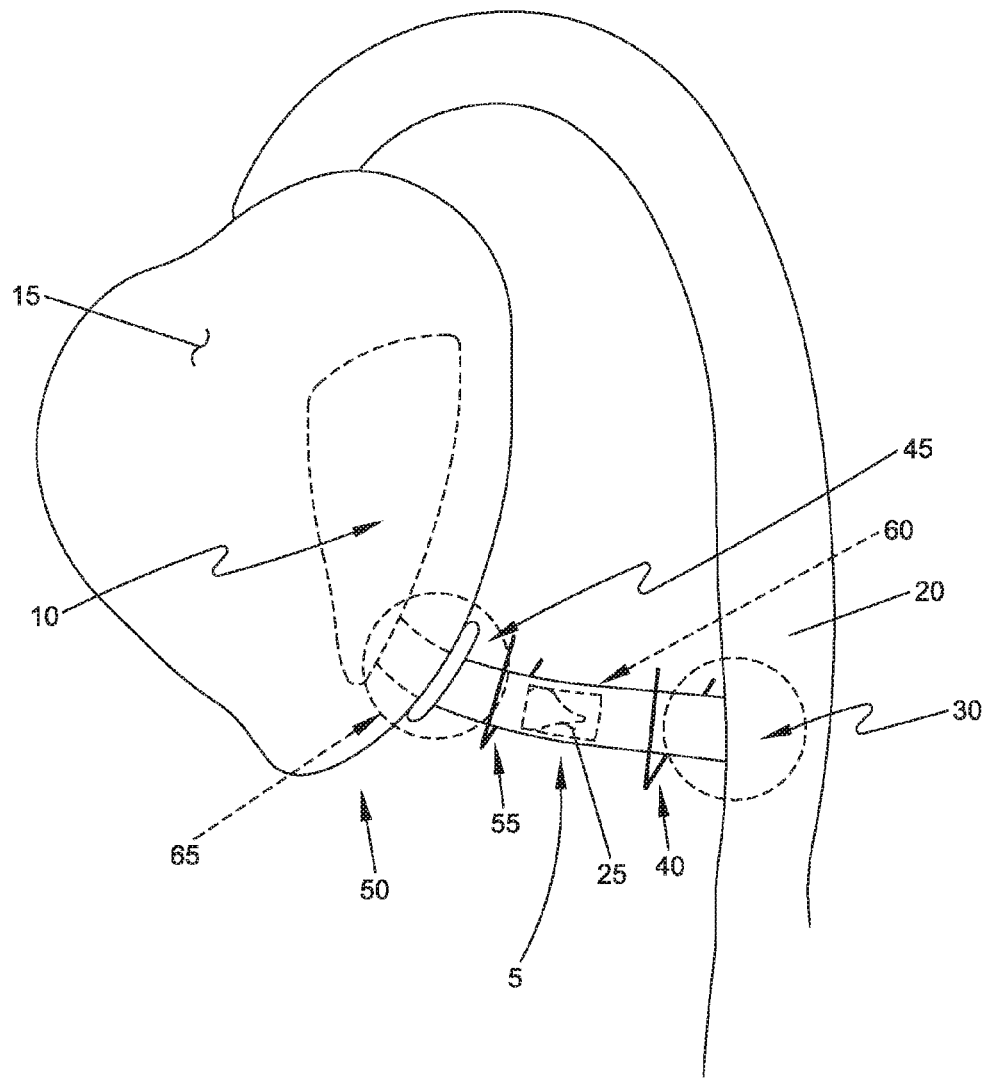
FIG. 2 is a schematic view showing a percutaneous aortic valve bypass.
Figure 3:
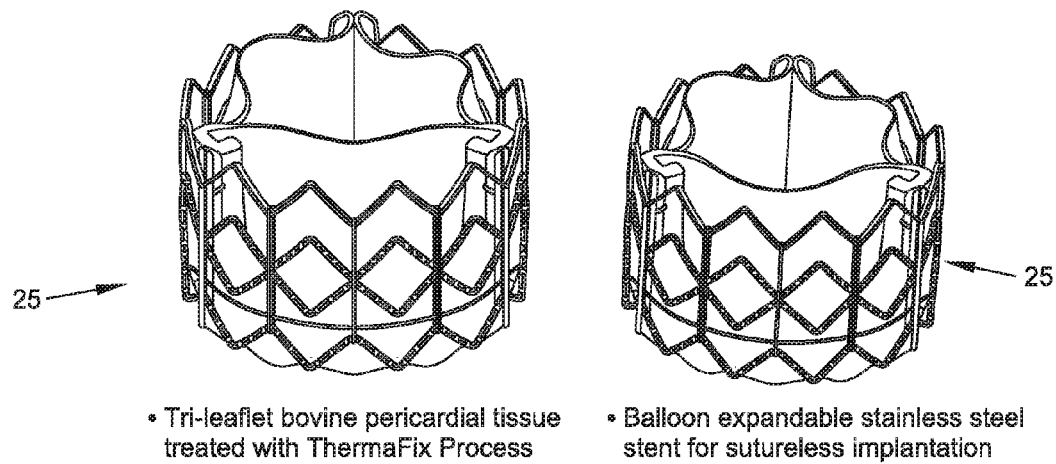
FIG. 3 is a schematic view showing exemplary percutaneous aortic valves.

In accordance with the present invention, there is provided a novel method and apparatus for effecting a percutaneous aortic valve bypass, which is an improved procedure that combines the best attributes of both aortic valve bypass and percutaneous valve therapy (PVT). More particularly, and looking now at FIGS. 2 and 3, with the novel percutaneous aortic valve bypass of the present invention, a bypass conduit 5 is deployed so that it extends between the left ventricle 10 of the heart 15 and the descending aorta 20, and a percutaneous valve 25 is endoluminally deployed in bypass conduit 5 between the left ventricle and the descending aorta. Bypass conduit 5 provides for fluid flow from the left ventricle to the descending aorta, and percutaneous valve 25 ensures that fluid flows only toward the descending aorta and prevents return flow back toward the left ventricle.

In one preferred form of the present invention, the percutaneous aortic valve bypass is performed in the following manner:

1. A "distal anastomosis" 30 is performed on the descending aorta, i.e., the distal end of bypass conduit 5 is attached to descending aorta 20. Hemostasis is maintained between bypass conduit 5 and descending aorta 20 so that blood cannot pass from the descending aorta into the bypass conduit. By way of example but not limitation, bypass conduit 5 is clamped immediately proximal (i.e., "heart side") to the distal anastomosis site with a clamp 40.

2. A "proximal anastomosis" 45 is performed in the vicinity of the apex 50 of the heart so as to connect the proximal end of bypass conduit 5 to left ventricle 10. Hemostatis is maintained between bypass conduit 5 and left ventricle 10 so that blood cannot pass from the left ventricle into the bypass conduit. By way of example but not limitation, bypass conduit 5 is clamped immediately distal (i.e., "aorta side") to the proximal anastomosis site with a clamp 55.

3. The hemostasis previously established between bypass conduit 5 and descending aorta 20 is removed so that the interior of the bypass conduit may be accessed via the descending aorta. By way of example but not limitation, where bypass conduit 5 was previously clamped with a clamp 40 to establish hemostasis immediately proximal to the distal anastomosis 30, the clamp 40 is removed.

Figure 4:
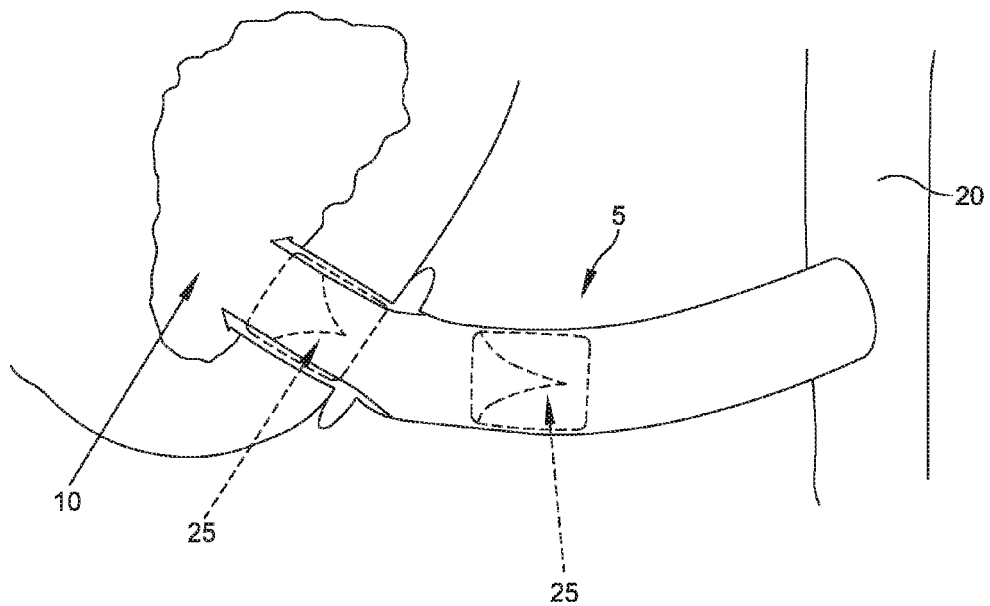
FIG. 4 is a schematic view showing possible locations for percutaneous valve deployment in the bypass conduit.

4. Percutaneous valve 25 is endoluminally deployed in the bypass conduit somewhere between the interior of left ventricle 10 and descending aorta 20. See, for example, FIG. 4, which shows several possible deployment sites for percutaneous valve 25, e.g., in the middle portion of the bypass conduit, or adjacent to the wall of the left ventricle, etc. Percutaneous valve 25 is oriented so that blood is able to flow away from the left ventricle, and prevented from flowing back toward the left ventricle.

5. The hemostasis previously established between left ventricle 10 and bypass conduit 5 is removed, so that blood may now flow from the left ventricle to the descending aorta via the bypass conduit, with percutaneous valve 25 preventing regurgitation. By way of example but not limitation, where bypass conduit 5 was previously clamped with a clamp 55 to establish hemostasis immediately distal to the proximal anastomosis 45, the clamp 55 is removed.

Significantly, the heart is beating throughout the foregoing percutaneous aortic valve bypass procedure.

Figure 5:
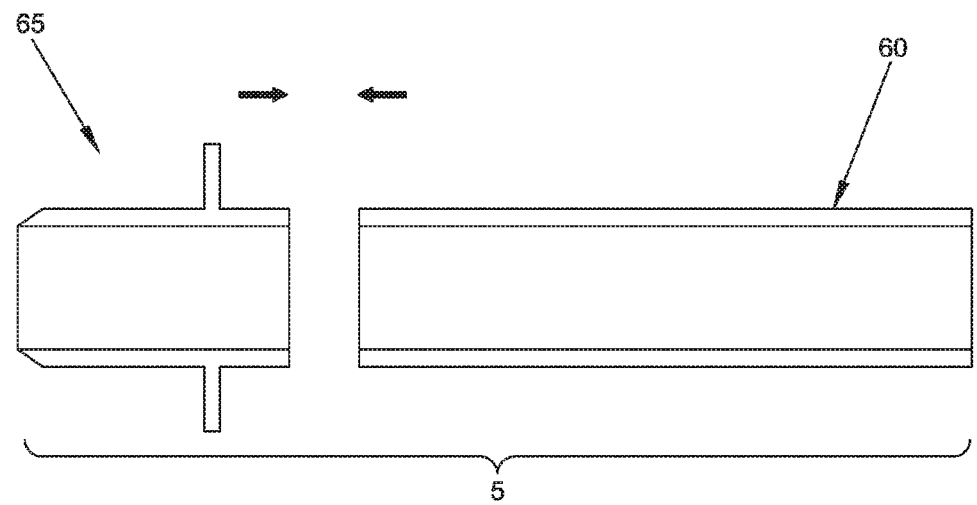
FIG. 5 is a schematic view showing a bypass conduit comprising a descending aorta connector and a left ventricle connector.

In one preferred form of the invention, and looking now at FIG. 5, bypass conduit 5 comprises a descending aorta connector 60 and a left ventricle connector 65, with descending aorta connector 60 being configured for connecting to descending aorta 20 on one end and to left ventricle connector 65 on the other end, and with left ventricle connector 65 being configured for connecting to left ventricle 10 on one end and to descending aorta connector 60 on the other end. In this form of the invention, descending aorta connector 60 is first connected to descending aorta 20 and hemostasis established at the distal anastomosis site; left ventricle connector 65 is connected to left ventricle 10 and hemostasis established at the proximal anastomosis site; descending aorta connector 60 is connected to left ventricle connector 65; hemostasis is removed at the distal anastomosis site; percutaneous valve 25 is deployed in the bypass conduit; and then hemostasis is removed at the proximal anastomosis site, whereby to complete the percutaneous aortic valve bypass procedure.

The order of the percutaneous aortic valve bypass procedure can vary somewhat from that described above, depending on device details and physician preference. By way of example but not limitation, the proximal anastomosis can be performed first and the distal anastomosis can be performed second. However, and as will be apparent to those skilled in the art, appropriate hemostasis must be maintained at appropriate times during the percutaneous aortic valve bypass procedure.

Some Possible Aspects and/or Variations in the Percutaneous Aortic Valve Bypass Some possible aspects and/or variations in the aforementioned preferred form of the invention include:

A. At the proximal (i.e., "heart side") anastomosis 45: a hole is formed in the wall of the left ventricle primarily by dilation.

B. At the proximal anastomosis 45: a hole is formed in the wall of the left ventricle primarily by cutting a muscle plug.

C. At the proximal anastomosis 45: a hole is formed in the wall of the left ventricle by cutting a muscle plug, and then by dilation of the cut hole. See, for example, the aforementioned U.S. Pat. No. 7,510,561.

D. At the distal (i.e., aorta side) anastomosis 30: various constructions may be used to facilitate securing the bypass conduit to the descending aorta—see, for example, (i) U.S. patent application Ser. No. 11/300,589, filed Dec. 15, 2005 by James Alan Crunkleton et al. for APPARATUS AND METHOD FOR CONNECTING A CONDUIT TO A HOLLOW VESSEL, published as U.S. Patent Publication No. 2006/0161193 on Jul. 20, 2006; (ii) U.S. Provisional Patent Application Ser. No. 61/281,591, filed Nov. 19, 2009 by Richard M. Beane et al. for APPARATUS AND METHOD FOR CONNECTING A CONDUIT TO A HOLLOW VESSEL, (iii) U.S. Provisional Patent Application Ser. No. 61/304,043, filed Feb. 12, 2010 by Richard M. Beane et al. for APPARATUS AND METHOD FOR CONNECTING A CONDUIT TO A HOLLOW VESSEL; and (iv) U.S. Provisional Patent Application Ser. No. 61/222,183, filed Jul. 1, 2009 by Richard M. Beane et al. for DISTAL ANATOMOSIS USING A T STENT, which four (4) patent applications are hereby incorporated herein by reference.

Figure 6:
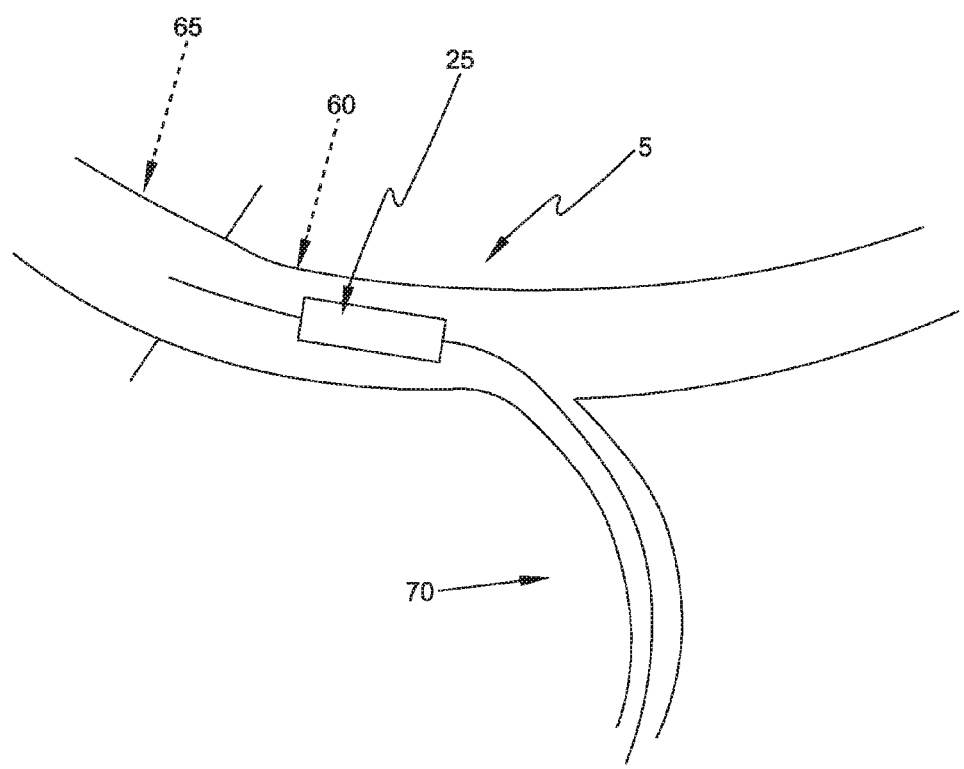
FIG. 6 is a schematic view of a bypass conduit comprising a side branch.

E. Bypass conduit 5 may contain a side branch 70 communicating with the interior of the bypass conduit. See FIG. 6. Side branch 70 may be used for installation of the percutaneous valve 25, and/or for installation of left ventricle connector 65 (where one is used). After use, side branch 70 may be permanently closed off, e.g., by means of a clamp or clip, a suture line, a staple, etc.

F. At Step 1 and/or 2 above—the overall length of bypass conduit 5 is adjusted to fit the patient. Typically, one end of a portion of the bypass conduit is shortened by cutting off a length of the bypass conduit.

G. At Step 4 above—percutaneous valve 25 is inserted into the femoral artery, moved proximally through the thoracic artery, moved through the distal anastomosis in the descending aorta, and then deployed in the bypass conduit somewhere between the interior of the left ventricle and the descending aorta.

H. At Step 4 above—percutaneous valve 25 is inserted through a thoracotomy into the bypass conduit or a side branch thereof.

In one form of the invention, where bypass conduit 5 comprises a descending aorta connector 60 and a left ventricle connector 65, the percutaneous valve is deployed within the descending aorta connector, or the percutaneous valve is deployed within the left ventricle connector.

In the foregoing description of a preferred form of the invention, reference is made to means for selectively preventing blood flow through the bypass conduit. These means can include, but are not limited to: application of a cross clamp on the bypass conduit, or disposition of a balloon occlusion device within the bypass conduit.

The Provision of Improved Surfaces to Enable Successful Deployment of a Percutaneous Valve within the Bypass Conduit Percutaneous valves were designed to be deployed into vascular tissue that (i) has appreciable radial compliance, and (ii) is penetrable by spikes, barbs or other anchoring means associated with the percutaneous valve. These aspects of percutaneous valve design will now be discussed in further detail.

1. The vascular tissue has appreciable radial compliance, i.e., the tissue is not rigid or stiff. For a non-self-expanding valve such as the Edwards SAPIEN valve, this allows the metallic stent structure of the percutaneous valve to be temporarily expanded (e.g., by a balloon) to a diameter greater than the final deployed diameter. When the expanding means (e.g., the balloon) is removed, the valve diameter is slightly reduced by pressure from the tissue surrounding the deployed valve. A small radial interface pressure remains between the valve outer diameter (OD) and tissue inner diameter (ID) after valve deployment. This radial interface pressure is critical to sealing paravalvular leaks. For a self-expanding valve, such as the CoreValve ReValving System, local tissue compliance aids in eliminating paravalvular leaks.

2. The vascular tissue is penetrable by spikes, barbs or other anchoring means associated with the percutaneous valve. These features on the OD of the valve are critical in preventing subsequent valve migration due to the pressure difference across the valve.

However, the surfaces of conventional bypass conduits are not conducive to secure valve seating, since they are neither appreciably radially compliant nor are they penetrable by spikes, barbs or other anchoring means associated with the percutaneous valve. As a result, it is difficult to achieve solid anchoring, and adequate paravalvular sealing, for percutaneous valves with conventional bypass conduits due to the materials used to form the bypass conduits. This is because existing bypass conduits are typically constructed out of radially stiff or inextensible materials such as woven polyester, polypropylene, titanium, and stainless steel.

Consequently, a need exists for bypass conduits to have improved inner surfaces to facilitate proper seating of the percutaneous valve therewithin.

Figure 7:
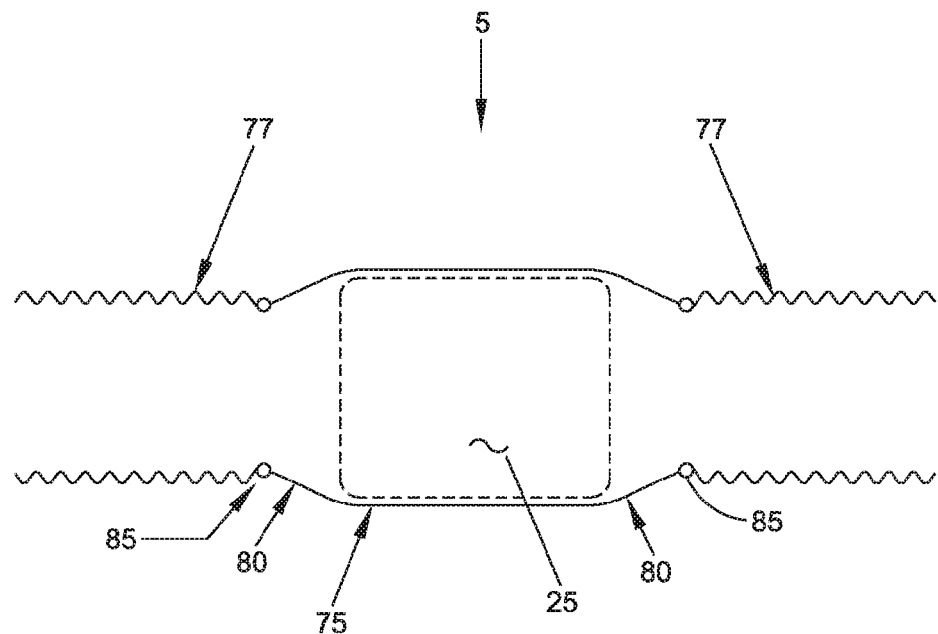
FIGS. 7-9 are schematic views showing various constructions wherein the bypass conduit comprises a radially compliant material for providing an improved seat for the percutaneous valve.

Modifications to the inner surface of a bypass conduit so as to provide for better retention and sealing of the percutaneous valve include:

1. The incorporation of a section of radially compliant material 75 (FIG. 7) into the length of bypass conduit 5. By way of example but not limitation, a section of Vascutek GelSoft™ knitted polyester fabric 75 (i.e., the "radially compliant material") is provided in a bypass conduit 5 constructed primarily of Vascutek GelWeave™ polyester woven fabric 77 (which is not appreciably radially compliant). When deployed into the GelSoft™ knitted polyester fabric (i.e., the radially compliant material) section of the bypass conduit, percutaneous valve 25 stretches the knitted polyester fabric 75 outwardly to a greater diameter. The knitted polyester fabric 75 has enough radial spring force to maintain adequate interface pressure against the percutaneous valve. Also, the bypass conduit is preferably provided with a reduced diameter (e.g., at 80) just distal to, and possibly also just proximal to, the valve seat so as to help lock the valve in place within the bypass conduit, thereby further preventing valve migration. This reduced diameter is preferably provided by sutures 85 tightened about the outer diameter of the bypass conduit. The relatively coarse knit of this radially compliant fabric 75 also enables any barbs on the percutaneous valve to anchor securely into the fabric.

Figure 8:
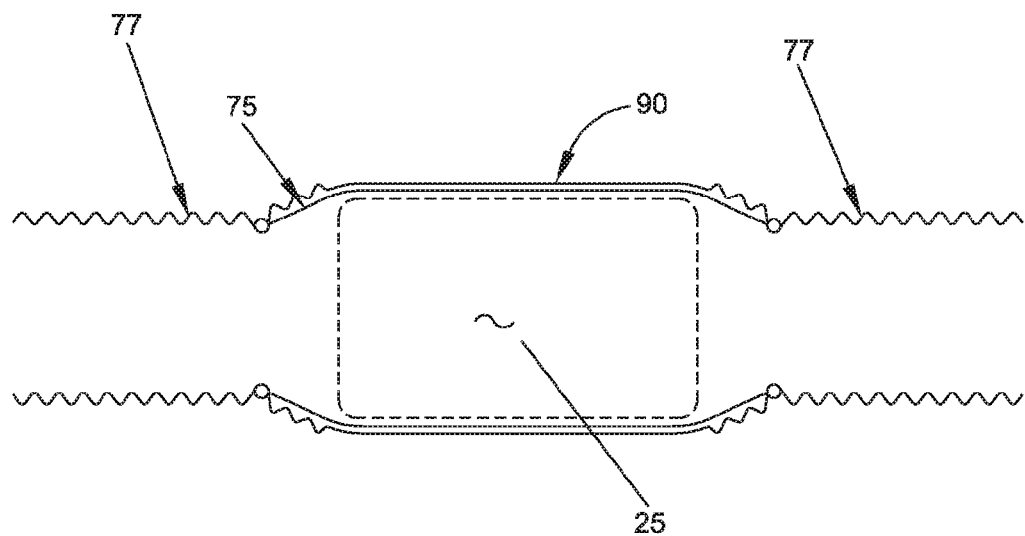

2. The configuration (1) immediately above, plus the provision of an additional sleeve 90 (FIG. 8) disposed coaxial with the section of radially compliant material (e.g., the knitted polyester fabric) 75. In one embodiment, sleeve 90 is disposed outside the section of radially compliant material (e.g., the knitted polyester fabric) 75 so that the radially compliant material is disposed inboard of sleeve 90—the additional sleeve 90 limits expansion in this section of the bypass conduit (i.e., it limits expansion of the radially compliant material), and also aids in hemostasis. This additional sleeve 90 can be made by thermoforming a section of GelWeave™ crimped woven polyester fabric on an expandable mandrel at an elevated temperature.

Figure 9:
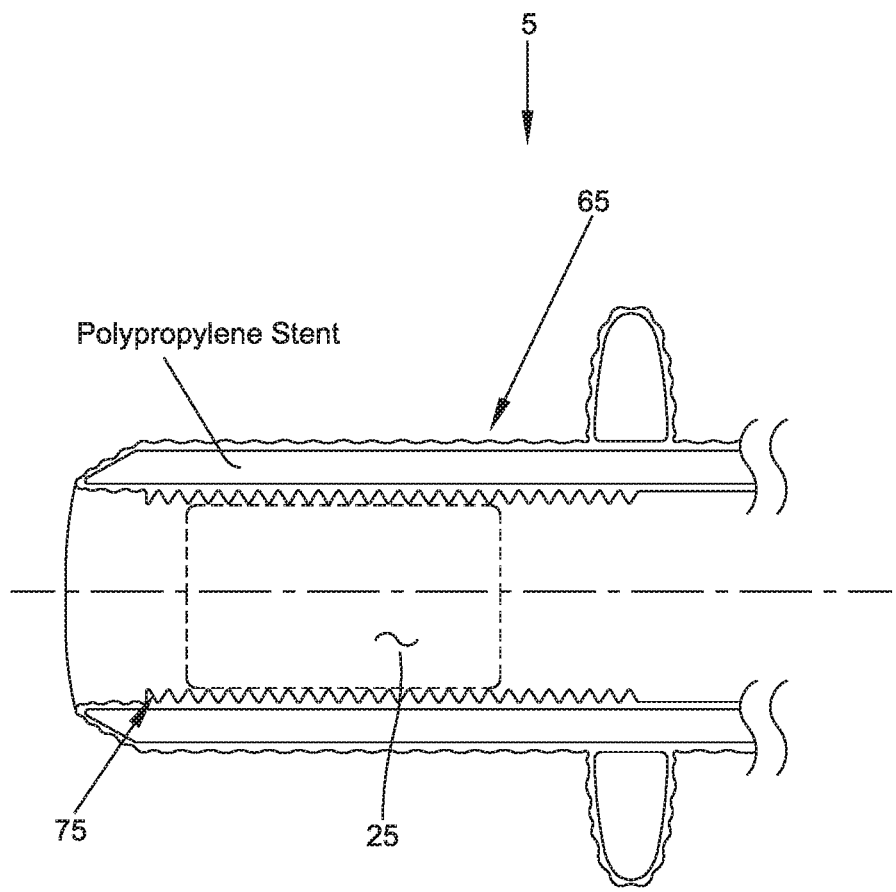

3. The incorporation of a section of compressed crimped knitted graft material 75 (i.e., radially compliant material) on the interior wall of bypass conduit 5. See FIG. 9. A high linear density of folds serves to: (a) provide radial compliance and an interface pressure; (b) provide many places for spikes to lock into; and (c) aid in sealing around the valve. This section of graft could be created by running sutures (e.g., 8 suture) axially through a stack of compressed crimped graft material so as to form the desired structure of radially compliant material.

4. Any of the aforementioned configurations may be practiced with a variety of bypass conduit constructions, e.g., they may be practiced where bypass conduit 5 comprises a single structure, or where bypass conduit 5 is a composite of a descending aorta connector 60 and a left ventricle connector 65. In this respect it should be appreciated that the aforementioned configurations 1-3 can be highly advantageous where bypass conduit 5 comprises a descending aorta connector 60 and a left ventricle connector 65, inasmuch as it may be desired to position the percutaneous valve 25 in the left ventricle connector 65, and the left ventricle connector 65 may be formed at least in part out of polypropylene stent (see FIG. 9), in which case the polypropylene stent with radially compliant material 75 will still provide a receptive environment for seating the percutaneous valve.

Further Modifications

It will be understood that many additional changes in the details, materials, steps and arrangements of parts, which have been herein described and illustrated in order to explain the nature of the invention, may be made by those skilled in the art while remaining within the principles and scope of the present invention.

What is claimed is:

1. A method for performing a percutaneous valve bypass, the method comprising:
    providing a bypass conduit comprising a single structure comprising a first end, a second end and a hollow lumen extending between the first end and the second end, wherein the single structure of the bypass conduit comprises a first segment formed out of a substantially radially non-compliant material and a second segment formed out of a substantially radially compliant material such that the hollow lumen is formed by both the substantially radially non-compliant material and the substantially radially wherein the second segment is positioned within a lumen of the first segment compliant material;
    connecting the first end of the bypass conduit to the left ventricle of the heart at a first anastomosis;
    maintaining hemostasis between the left ventricle of the heart and the bypass conduit so that fluid cannot pass from the left ventricle of the heart into the bypass conduit;
    connecting the second end of the bypass conduit to the descending aorta at a second anastomosis;
    endoluminally advancing a percutaneous valve through the descending aorta, into the bypass conduit and to a deployment site located within the second segment of the bypass conduit, wherein the second segment of the bypass conduit comprises a reduced diameter section distal to the deployment site to prevent valve migration;
    deploying the percutaneous valve at the deployment site so that fluid is permitted to pass from the left ventricle side of the valve to the descending aorta side of the valve but is prevented from passing from the descending aorta side of the valve to the left ventricle side of the valve; and
    removing hemostasis between the left ventricle and the bypass conduit so as to permit fluid to flow from the left ventricle, through the percutaneous valve and into the descending aorta.

2. A method according to claim 1 wherein a second hemostasis is established at the second anastomosis after connecting the second end of the bypass conduit to the descending aorta.

3. A method according to claim 2 wherein the second hemostasis is released at the second anastomosis after the percutaneous valve has been deployed at the deployment site.

4. A method according to claim 1 wherein the radially non-compliant material comprises a woven material.

5. A method according to claim 4 wherein the woven material comprises at least one selected from the group consisting of woven polyester and woven polypropylene.

6. A method according to claim 1 wherein the radially compliant material comprises a knitted material.

7. A method according to claim 6 wherein the knitted material comprises a knitted polyester.

8. A method according to claim 1 wherein the second segment is disposed longitudinally adjacent to the first segment.

9. A method according to claim 1 wherein the bypass conduit comprises a side branch communicating with an interior portion of the bypass conduit.

10. A method according to claim 9 wherein the percutaneous valve is advanced through the side branch to gain entry into the bypass conduit.

11. Apparatus for performing a percutaneous valve bypass, the apparatus comprising:
    a bypass conduit comprising a single structure comprising a first end for connection to a left ventricle of a heart, a second end for connection to a descending aorta and a hollow lumen extending between the first end and the second end, wherein the single structure of the bypass conduit comprises a first segment formed out of a substantially radially non-compliant material and a second segment formed out of a substantially radially compliant material such that the hollow lumen is formed by both the substantially radially non-compliant material and the substantially radially compliant material wherein the second segment is positioned within a lumen of the first segment; and
    a percutaneous valve for disposition at a deployment site located within the second segment of the bypass conduit so that fluid is permitted to pass from the left ventricle of the heart to the descending aorta but is prevented from passing from the descending aorta to the left ventricle of the heart;

wherein the percutaneous valve is configured to be disposed at the deployment site located within the second segment of the bypass conduit after the first end of the bypass conduit has been connected to the left ventricle of the heart and after the second end of the bypass conduit has been connected to the descending aorta by endoluminally advancing the percutaneous valve through the descending aorta, into the bypass conduit and to the deployment site located within the second segment of the bypass conduit, wherein the second segment of the bypass conduit comprises a reduced diameter section distal to the deployment site to prevent valve migration.

12. Apparatus according to claim 11 wherein the radially non-compliant material comprises a woven material.

13. Apparatus according to claim 12 wherein the woven material comprises at least one selected from the group consisting of woven polyester and woven polypropylene.

14. Apparatus according to claim 11 wherein the radially compliant material comprises a knitted material.

15. Apparatus according to claim 14 wherein the knitted material comprises a knitted polyester.

16. Apparatus according to claim 11 wherein the second segment is disposed longitudinally adjacent to the first segment.

17. Apparatus according to claim 11 wherein the bypass conduit comprises a side branch communicating with an interior portion of the bypass conduit.

18. Apparatus according to claim 17 wherein the side branch is sized to permit the percutaneous valve to move through the side branch and into the bypass conduit.

19. A method according to claim 1 wherein the second segment is disposed coaxial with the first segment.

20. Apparatus according to claim 11 wherein the second segment is disposed coaxial with the first segment.

* * * * *